(12) United States Patent
Grisé

(10) Patent No.: US 9,408,894 B2
(45) Date of Patent: Aug. 9, 2016

(54) ANTI-FATIGUE COMPOSITION

(71) Applicant: Michel Grisé, Mont St-Hilaire (CA)

(72) Inventor: Michel Grisé, Mont St-Hilaire (CA)

(73) Assignee: Michel Grise, St-Hilaire, Quebec (CA)

( * ) Notice: Subject to any disclaimer, the term of this patent is extended or adjusted under 35 U.S.C. 154(b) by 34 days.

(21) Appl. No.: 14/010,005

(22) Filed: Aug. 26, 2013

(65) Prior Publication Data

US 2013/0344179 A1 Dec. 26, 2013

Related U.S. Application Data

(63) Continuation of application No. 12/929,903, filed on Feb. 23, 2011, now abandoned.

(60) Provisional application No. 61/338,673, filed on Feb. 23, 2010.

(51) Int. Cl.
*A61K 36/45* (2006.01)
*A61K 36/886* (2006.01)
*A61K 36/00* (2006.01)
*A61K 38/39* (2006.01)
*A61K 36/484* (2006.01)

(52) U.S. Cl.
CPC ............... *A61K 38/39* (2013.01); *A61K 36/45* (2013.01); *A61K 36/484* (2013.01)

(58) Field of Classification Search
CPC .. A61K 2800/00; A61K 36/45; A61K 36/484
See application file for complete search history.

(56) References Cited

U.S. PATENT DOCUMENTS

| | | |
|---|---|---|
| 2002/0025310 A1 | 2/2002 | Bland |
| 2005/0256192 A1 | 11/2005 | Gardiner et al. |
| 2007/0031518 A1 | 2/2007 | Randolph et al. |
| 2007/0154575 A1* | 7/2007 | Shimoda et al. ............ 424/756 |
| 2009/0005322 A1* | 1/2009 | Purpura et al. .............. 514/21 |

FOREIGN PATENT DOCUMENTS

| | | |
|---|---|---|
| JP | 2002173422 | 6/2002 |
| WO | 2004049830 | 6/2004 |

OTHER PUBLICATIONS

Reid (2008) Free Radical Biology & Medicine 44: 169-179.*
Clark et al. (2008) Curr. Med. Res. Opin. vol. 24, No. 5, pp. 1485-1496.*
Ding et al. (2011) Food Hydrocolloids 25: pp. 1350-1353.*
Dulebohn et al. (2008) J. Agric. Food Chem. 56: 11700-11706.*
Fuhrman et al. (2002) Nutrition 18: 268-273.*
Huo et al. (2011) Int. J. Mol. Sci. 12: 6529-6543.*
Kalt et al. (2000) J. Food Science vol. 65, No. 3, 390-393.*
Liu et al. (2011) Asian J Animal Veterinary Adv. 6(12): 1214-1223.*
Smith et al. (2000) J. Food Science vol. 65, No. 2 pp. 352-356.*
Vaya et al. (1997) Free Radical Biol & Med. vol. 23, No. 2, pp. 302-313.*
Vina et al. (2000) Life, 50: 271-277.*
Yoon et al. (2005) Yonsei Medical Journal vol. 46, No. 5, pp. 585-596.*
MacRae et al. (2006) Int. J. Sport Nutr. Exerc. Metabol. 16, 405-419.*
Wheeler et al. (1999) Cell. Mol. Life Sci. 56, 843-856.*
Kim et al. (2006) Biochem. Biophys. Res. Comm. 345, pp. 1215-1223.*
Torri et al. (2007) J. Pharmacy and Pharmacology, 59 pp. 591-596.*
Dybka et al. (2009) Food Chemistry and Biotechnology, vol. 73.*
Powers et al. (2004) J. Sports Sciences, 22, 81-94.*
Bello et al. (2006) Current Medical Research and Opinion, vol. 22, No. 11, 2221-2232.*
Cao et al. (1999) J. Appl. Physiol. 86(60: 1817-1822.*
Fuhrman et al. (1997) Am. J. Clin. Nutr. 66: 267-275.*
Gordon et al. (1995) J. Agric. Food Chem. 43, 1784-1788.*
Li et al. (2013) Food Research International 51: 283-293.*
Thomas et al. (2007) Int. J. Sports Med. 28: 703-713.*
Urso et al. (2003) Toxicology 189: 41-54.*
K.A, Youdim et al.(2002), Potential role of dietary flavonoids in reducing microvascular endothelium vulnerability to oxidative and inflammatory insults, Journal Nutritional Biochemistry13, pp. 282-288.
J. Vaya et al. (1997), Antioxydant constituents from Licorice roots: isolation, structure elucidation and antioxidative capacity toward LDL oxidation, Free Radical Biology and Medicine vol. 23, No. 2, pp. 302-313.
E. Torri et al. (2007), Anti-inflammatory and antinociceptive poperties of blueberry extract (*Vaccinium corymbosurn*) Journal of Pharmacy and Pharmacology 59: pp. 591-596.
B. Shukitt-Hale et al. (2005) Dietary supplementaton with fuit polyphenolics ameliorates age-elated defcits in behavior and neuronal markers of inflammation and oxidative stress, Age 27: pp. 49-57.
B. Fuhrman et al. (1997), Licorice extract and its major poiyphenal glabridin protect low-density lipoproteinagainst lipid peroxidation; in vitro and ex vivo studies in humans and in atherosclerotic apolipoprotein E-deficient mice , the American journal of Clinical Nutrition, 66:pp. 267-275.
J.A. Bralley et al,(1994), Treatment of chronic fatigue syndrome with specific amino acid supplementaton, journal of Applied Nutrition, vol. 46, No. 3 pp. 74-78.
Author Bhagat Bhagavanadasa Title of publication—Rasarajamahaudadhi(part-5) Page(s) being submitted—06 (p. 04-09) Publication Date—Oct. 2008 Publisher—Khemraj Srikrishnadas, Srrivyankateshwar press Place of Publication—Mumbai, India.†

(Continued)

*Primary Examiner* — Chris R Tate
*Assistant Examiner* — Russell Fiebig
(74) *Attorney, Agent, or Firm* — Benoit & Cote Inc.

(57) ABSTRACT

The present invention relates to a food supplement composition for reducing fatigue, and/or improving recovery and resistance to fatigue. The composition comprised of collagen hydrolysate, blueberry extract and liquorice extract.

6 Claims, 2 Drawing Sheets

(56) References Cited

OTHER PUBLICATIONS

Author Govinda Dasa Title of publication—Bhaisajya Ratnavali Page(s) being submitted—06 (p. 10-15) (ref. pg. No. of publication: 766) Publication date—Edn. 14th. 2001 Publisher—Chaukhamba Sanskrit SansthanVaranasi Place of Publication—Varanasi, India.†

Author Agnivesa Title of Publication—Caraka Samhita vol. II Pages(s) being submitted—07 (p. 16-22) (Ref. p. No. of publication:184) Publication Date—Edn. 5th. 2000. Publisher—Chaukhamba Orientalia Place of Publication—Varanasi, India.†

\* cited by examiner
† cited by third party

ANTI-FATIGUE COMPOSITION

CROSS-REFERENCE TO RELATED APPLICATIONS

This application is filed under 37 CFR 1.53(b) as a continuation application. This application claims priority under 35 USC §120 of U.S. patent application Ser. No. 12/929,903 filed on Feb. 23, 2011, which claims priority of U.S. Provisional Application No. 61/338,673, filed Feb. 23, 2010, the specifications of which are hereby incorporated by reference in their entirety.

BACKGROUND OF THE INVENTION a) Field of the Invention present invention relates to compositions for enhancing the fatigue resistance or to reduce the fatigue level of an individual. More specifically, the present invention relates to a composition and a method comprising a synergistic combination of antioxidant and blueberry extracts for enhancing the fatigue resistance or to reduce the fatigue level.

b) Description of the Prior Art

This section describes background subject matter related to the disclosed embodiments of the present invention. There is no intention, either express or implied, that the background art discussed in this section legally constitutes prior art.

Fatigue is an important factor that influences physical performance. It has two components, central fatigue and peripheral fatigue. Central fatigue has been described in the art as relating to neuronal inputs to muscle and the brain circuitry that drives them. Peripheral fatigue relates to nutritional, hormonal, and mechanical aspects of metabolism and physiology that directly affect muscle tissue. Dietary amino acids and protein have been examined for their affect on peripheral and central fatigue, particularly from the metabolic and neurochemical perspectives. Fernstrom and Wolfe, Introduction to symposium on branched-chain amino acids in exercise, J. of Nutrition 136: 524S (2006).

PCT Patent Publication Number WO 2004/049830, published Jun. 17, 2004 by applicant Tsuchita et al., describes an improver of muscular fatigue comprising 4 kinds of amino acids (leucine, isoleucine, valine and glutamine), and a whey protein component (whey protein and/or decomposition product of whey protein). At least one of a whey protein isolate (WPI), a whey protein concentrate (WPC), beta-lactoglobulin, and alpha-lactalbumin is used as the whey protein.

Citrulline malate is another anti-fatigue substance that has been described in the art. It has been suggested to have a protective effect against acidosis and ammonia poisoning, which may explain its anti-fatigue properties. Activity of citrulline malate on acid-base balance and blood ammonia and amino acid levels.

Japanese Patent Application Number JP1988000281672, published May 17, 1990 by Hiroko et al., describes an amino acid-containing food composition without the bitter taste stemmed from the amino acids. The composition described contains (A) amino acids(s) (pref. isoleucine, leucine, lysine, methionine, phenylalanine, tryptophan, valine, arginine, histidine, citrulline, omithine or proline) and/or peptide, and (B) tea and/or the flavoring component(s) thereof. The disclosure teaches that it is preferable that the amino acid concentration be 0.1 to 60 wt % and the concentration of the tea and/or the flavoring component(s) thereof be 0.1 to 50 wt % in the final product.

Chinese Patent Application Number CN2003000117070, published Oct. 29, 2003 by applicants Qi and Jie, discloses a medical composition for treating various ailments, including chronic fatigue, which is prepared from ornithine and citrulline or their salts, jujube, ginkgo seed and ginseng.

U.S. Patent Publication No. 2005/0256192, published Nov. 17, 2005 by applicant Gardiner and Heuer describes a nutritional composition for enhancing lean muscle stimulus, growth, strength and recovery, supporting endurance, strength, performance, size and stamina in individuals. The nutritional composition may include L-arginine and creatine. In addition, the nutritional composition may also include L-citrulline, L-aspartic acid, ginseng root extract, and maritime pine (bark) extract or it may also include L-leucine and L-valine.

On the other hand, although nourishing drinks that have been widely used conventionally for recovery from fatigue contain, as main ingredients, various kinds of vitamins, caffeine, taurine and the like no ingredients other than caffeine exhibit a distinct effect for recovery from fatigue. Further, as for Asian ginseng, royal jelly and propolis protein, even when an effect is recognized, the active site (here, the term "active site" referring to a biochemical target of a potent ingredient, e.g., a specific enzyme) is not clear. In addition, all of these products have a large problem with regard to sensory feeling, and it is believed that use of them in a form other than that of a pharmaceutical is rather difficult and their frequent use in everyday dietary life is difficult.

On the other hand, it is known that anserine and carnosine contained in large quantities in seafood and animal meat activate ATPase, and JP-A-2002-173422 discloses that an enhancement of exercise capacity and anti-fatigue effect are exhibited by administrating at least one kind selected from imidazole peptides, especially anserine, carnosine and balenine obtained by purifying specifically lower molecular fractions of extracts of seafood, chicken meat, animal meat or the like, by allowing them to run through an ultra filter membrane. However, there is disclosed no discussion of the amount of ATP that is important upon recovery from fatigue after an exercise load, and therefore the relationship between administration and recovery from fatigue is not clear.

Considering the state of the art described above, it would be highly desirable to be provided with a new composition for reducing fatigue, improving resistance to fatigue, or improving recovery to fatigue.

SUMMARY OF THE INVENTION

One aim of the present invention is to provide a food supplement composition for reducing fatigue, said composition comprising collagen hydrolysate, blueberry extract, and licorice extract.

Another aim of the present invention is to provide a dietary supplement comprising the composition according to the present invention.

The collagen hydrolysate may be of a molecular weight (Mw) lying in the range of from 500 to 15,000 Daltons.

Preferably, the collagen hydrolysate has a molecular weight (Mw) from 1,500 to 5,000.

Another aim of the present invention is to provide a food supplement composition comprising collagen hydrolysate in proportion of 0.1% (w/v or w/w) to 25% (w/v or w/w), a blueberry extract in proportion of 0.1% (w/v or w/w) to 20% (w/v or w/w), and a liquorice extract in proportion of 0.1% (w/v or w/w) to 30% (w/v or w/w).

Preferably, the food supplement composition of the present invention comprised of at least one amino acid. The amino acid can be anyone of known amino acid in the industry of health. For example, but not limited to, the amino acid can be a glycine, a lysine, an arginine, and/or a glutamine. The amino acid can be an analog of anyone of known amino acid as mentioned before. The food supplement composition of the invention may also comprised of at least two different amino acids or analogs thereof.

The food supplement composition may also comprised of a polyphenol compound from natural sources or synthesized. The polyphenol can be selected, without being limited to, the group of salicylate, analog or derivative thereof.

In accordance with the present invention there is provided a method for reducing fatigue, the method comprising orally administering to an individual the food supplement composition as described herein. The composition can be for example, but not limited to, administered at a rate of at least 1 gram or 1 ml per day, such as another example at a rate of about from 5 to 25 ml or gams per day.

The food supplement composition of the present invention can be orally given as well to a human individual as to an animal for at least one of reducing fatigue or improving the recovery and/or resistance to fatigue, or enhancing endurance to stress, fatigue and/or physical or psychological training or exercising.

For the purpose of the present invention the following terms are defined below.

The term "fatigue" is intended to mean, but is not limited to, the physiological states also called exhaustion, lethargy, languidness, languor, lassitude, listlessness, and awareness. It can describe a range of afflictions, varying from a general state of lethargy to a specific work-induced burning sensation within one's muscles. It can be both physical and mental. Physical fatigue is the inability to continue functioning at the level of one's normal abilities. It is ubiquitous in everyday life, but usually becomes particularly noticeable during heavy exercise. Mental fatigue, on the other hand, rather manifests in somnolence.

The expression "reducing fatigue" as used and claimed herein is intended to mean reducing after the fatigue body state has occurred, or preventing the fatigue. It is also intended to mean endurance and/or recovery enhancement or improvement to physical training, exercising or stress.

DESCRIPTION OF THE PREFERRED EMBODIMENT

Figure 1:
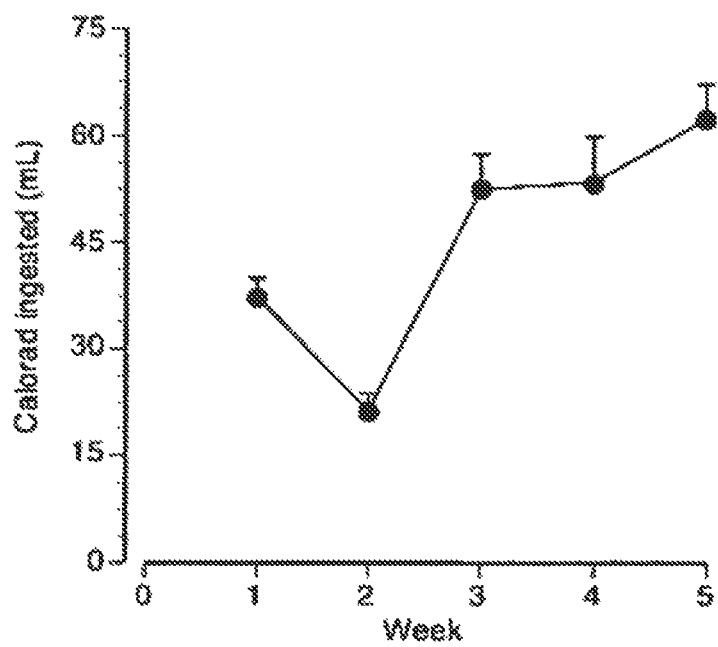
FIG. 1 illustrates the consumption by rats of Formula 3.

The present invention now will be described more fully hereinafter with reference to the accompanying drawings, in which preferred embodiments of the invention are shown. This invention, may, however, be embodied in many different forms and should not be construed as limited to the embodiments set forth herein; rather, these embodiments are provided so that this disclosure will be thorough and complete, and will fully convey the scope of the invention to those skilled in the art.

As a preface to the detailed description presented below, it should be noted that, as used in this specification and the appended claims, the singular forms "a", "an", and "the" include plural referents, unless the context clearly dictates otherwise.

In instances where the word "about" is used in this document, this indicates that the precision of a value is within about plus or minus 10%.

Disclosed herein is an oral composition which can be mixed into various liquids and soft foods to provide improved fatigue recovery or fatigue resistance, or endurance enhancer to physical or mental training or stress.

In accordance with the present invention, there is provided an composition for oral absorption comprising collagen hydrolysate, blueberry extract, and licorice extract. The invention composition can be supplemented by a specific blend of amino acids.

According to another embodiment of the invention, the composition of the present invention comprises between about 0.001 to 10% (w/w), but preferably between about 0.01 to 0.1% (w/w); between about 0.1 to 20% of blueberry extract, but preferably between about 1 to 10% (w/w); and between about 0.1 to 20% of licorice extract, but preferably 0.5 to 10% (w/w).

Disclosed herein is an oral composition which can be mixed into various liquids and soft foods to provide improved fatigue recovery or fatigue resistance, or endurance enhancer to physical or mental training or stress. The composition comprises a relatively high concentration of collagen hydrolysate, blueberry extract, and licorice extract.

Collagen hydrolysate is a denatured and partially hydrolyzed protein, which can be obtained for example, but not limited to, from collagenic substances of vertebrates, in particular, mammals, poultry or fish. Peptides having a different structure and also a different biological effect result from collagen hydrolysis. Collagen hydrolysate contains approximately twice as many of the amino acids lysine, glycine and glutamine as the average food protein. Collagen hydrolysate is also rich in the amino acids proline and hydroxyproline. Hydroxyproline has not been detected in any significant concentration in any other foodstuff. The above-mentioned amino acids are essential for the formation of mammal collagen, i.e., for the connective tissue metabolism, in particular, the bone and cartilage metabolism. According to the present invention, collagen hydrolysis is one of the ingredients of the present invention allowing to prevent and/or reducing fatigue of an individual.

The blueberry extract of the invention is intended to include whole blueberries or a part thereof. The whole blueberries can be processed by homogenization known in the art. The blueberry extract can be alternatively according to one embodiment of the invention the liquid part as well as the solid part of blueberries, or a mixture thereof. The blueberry extracted can be from the berries of different species, and are known as being of the genus *Vaccinium*. Other sections in the genus, native to other parts of the world including western North America, South America, Europe, and Asia, include other wild shrubs producing similar-looking edible berries such as huckleberries in (North America) and bilberries (Europe). These species are sometimes called "blueberries" and sold as blueberry jam or other products. Especially, blueberries contain anthocyanins, other antioxidant pigments and various phytochemicals possibly having a role in the present composition invention in at least one of reducing or preventing fatigue.

A blueberry extract of the invention can be standardized to at least 5% anthocyanosides.

The blueberry extract used according to the invention can be prepared as briefly described in the following.

Fresh blueberries can be pressed to obtain a blueberry juice concentrate which, subsequently, can be subjected to ultra filtration.

In accordance with another embodiment of the present invention, there is provided an anti-fatigue composition comprising at least one polyphenol compound.

Dried plant extract containing polyphenol, salicylates, or flavanoids is provided at levels of from 0.1 mg to 10 grams per kilogram body weight per day, preferably at levels of 10 mg to 1 gram per kilogram bodyweight per day, and above or an equivalent amount of a semi-dried or fully hydrated form of plant extract.

The polyphenol compound can be a polyphenolic acid, which is generally obtained from natural sources and plants, under form, for example but not limited to, plant extracts. Again for example, polyphenol can be obtained from liquorice, wintergreen, *betula, taxus, larix*, rosemary, grape seeds, or combination thereof.

Alternatively, the herbal phenol compound is provided as an extract from a plant. The phenol compound can be extracted and partially or fully purified from the herb.

Several phenol compounds extracted from plant extracts as disclosed above (and related family members such as oregano) have exhibited antioxidant effects. Phenols from plant extracts include, but are not limited to, carnosol, rosemanol, camosic acid and rosemaridiphenol. These phenol compounds may act as antioxidants, inhibit carcinogenesis or act as anti-inflammatory agents.

Plant extracts according to the invention may be in any form. It may be dried, fresh, crushed, in solution, in oil, as a powder, liquid (either as a solution or as an oil) or semi-solid.

Another aspect of the invention may optionally comprise proanthrocyanidins. The proanthrocyanidins of the present invention can be provided by natural or synthetic sources. The source of the proanthrocyanidins is not limiting. The proanthrocyanidins can also be provided by grape seed oil for example, without limiting the invention to this source.

Licorice extract, which provide antioxidant potentiating properties in the body is included in the composition. Licorice is a plant belonging to the genus *Fabaceae Glycyrrhiza* widely distributed in the People's Republic of China, Europe, Russian Federation, Republic of Afghanistan, Iran, Islamic Republic of Pakistan and the like. The roots thereof and the like have a long history of ingestion where they were utilized as a food or a crude drug. Since glycyrrhizin (glycyrrhizic acid), which is the main component of a water extract of licorice, has superior pharmacological actions such as an anti-inflammatory action, an antitumor action, an anti-allergic action and the like, it has been widely utilized for foods, pharmaceutical products, cosmetics and the like. In addition, since glycyrrhizin is about 200 times as sweet as sucrose, it is also used as a sweetener. In the US, licorice was registered as a GRAS (Generally Recognized As Safe) food by FDA in 1985.

Among others, liquorice has been shown to contain active salicylates and saponins including glycyrrhizin. These compounds have been reported to have liver-protective effects through their anti-free radical properties. Glycyrrhizin is converted into its aglycone by intestinal flora. Flavonoid aglycones are very bio-available.

The licorice polyphenol contained in the composition of the present invention is not particularly limited as long as it is a polyphenol component contained in the above-mentioned licorice. Specific examples thereof include glycycoumarin, glycerol, glycyrin, liquiritigenin, glicoricone, glabridin, glabrene, glabrol, 3'-hydroxy-4'-O-methylglabridin, 4'-O-methylglabridin, glyurallin B, licocoumarone, gancaonin I, dehydroglyasperin D, echinatin, isolicoflavonol, dehydroglyasperin C, glyasperin B, glycyrrhisoflavanone, lupiwighteone, glyasperin D, salicylates and derivatives or analogs thereof, semilicoisoflavone B and the like. The composition of the present invention contains at least one kind of licorice polyphenol from among such licorice polyphenol components. Among these, the composition of the present invention preferably contains at least any one kind of glabridin, glabrene, glabrol, 3'-hydroxy-4'-O-methylglabridin, 4'-O-methylglabridin and the like, and more preferably contains at least glabridin.

In another embodiment of the composition of the present invention, the composition contains licorice polyphenol and polyphenol other than licorice polyphenol. Examples of the polyphenol other than licorice polyphenol include genistein, daidzein, quercetin, rutin, catechin, epigallocatechin gallate, hesperidin, nobiletin, tyrosol, hydroxytyrosol, oleuropein, naringenin, caffeic acid, apple polyphenol, tea polyphenol, gallic acid and the like. Preferred are genistein, daidzein, quercetin, rutin, catechin, epigallocatechin gallate, hesperidin, nobiletin, naringenin, caffeic acid, apple polyphenol and tea polyphenol. These polyphenols may be used alone or in a mixture of two or more kinds thereof. Genistein here is polyphenol contained in leguminous plants such as soybean and the like.

According to one embodiment, the daily dose (effective intake) of the food supplement composition according to the present invention is set preferably at from 1 to 2000 ml or mg/70 kg-body weight. More specifically, the daily dose is set preferably at from 3 to 700 ml or mg/70 kg-body weight, more preferably from 5 to 500 ml or mg/70 kg-body weight, even more preferably from 10 to 50 ml or mg/70 kg-body weight.

According to another embodiment of the present invention, the composition may comprise polypeptides and/or amino acids. Polypeptides and amino acids of the kind which are related to reducing and/or preventing fatigue, or improving recovery from fatigue may be added optionally, for particular end use applications. Examples of polypeptides which may be added to the composition include glutamine peptides and hydrolyzed whey protein peptides having a molecular weight of less than about 10,000 Daltons (typically having a molecular weight ranging from about 1,000 to about 10,000 Daltons). Amino acids and their analogs and derivatives which may be added to the composition include glycine, lysine, L-lysine, L-arginine, phosphatidylcholine, Taurine, L-Glutamine, L-Arginine, L-Phenylalanine, L-Tyrosine, L-Citrulline, and N-acetylcysteine, by way of example and not by way of limitation. The concentration of amino acids and their analogs and derivatives in the composition ranges from about 0.01% by weight to about 15.0% by weight, more typically the concentration is in the range of about 0.11% by weight to about 11% by weight.

The food composition for recovery from fatigue according to the present invention may be compounded with suitable additives in such a range that the effect of the present invention is not jeopardized.

Examples of such additives include other nutritional components that promote the fatigue recovering effect such as carbohydrates (glucose, sucrose, starch etc.), lipids (vegetable oil, fish oil, animal fat etc.), proteins (soybean protein, milk protein etc.), minerals (inorganic salts such as potassium salt, sodium salt and calcium salt etc.), vitamins (thiamine, niacin, vitamin C, carotene etc.); anti-fatigue components such as taurine, caffeine etc.; taste-improving components such as sucrose, aspartame, acesulfame K, sodium glutamate, sodium chloride etc. suitable for imparting functions as a food (taste, eating feeling, safety etc.); excipients such as glycerin, gelatin or ahydrolysate thereof, carbohydrates, potassium sorbate, sodium benzoate, citric acid, inorganic or organic salts etc.; bacteriostatic components such as ethyl alcohol, acetic acid, sodium acetate, glycine etc. for a similar purpose; and pigments including pigments derived from natural products such as annatto pigment, safflower pigment, paprika pigment, beni-koji (red koji mold) pigment, grape pigment etc. and various synthetic pigments for a similar purpose. An additive is not limited to these, and other additives that are conventionally used in this field can also be compounded.

Various flavorings and sweeteners (preferably artificial sweeteners to reduce the amount of carbohydrates in the compound) may be added to provide palatability. For example, vanilla flavorings may be present at a concentration ranging from about 1% by weight to about 5% by weight. Artificial sweeteners may be present at a concentration ranging from about 0.1% by weight to about 1.0% by weight. In one embodiment artificial sweetener is present at about 0.11% by weight.

One skilled in the art of food and dietary supplements will recognize that there are a number of different flavorings and antioxidants which may be used in combination with the edible nutritional whey protein. In addition, there are a variety of polypeptides and amino acids which are known to be beneficial to the body and which may be added to the composition as well, for particular remedial health benefits. It is not intended that the scope of the invention be limited to the exemplary compositions described herein.

The nutritional composition according to the present invention manufactured in the above-described manner can be distributed without further modification, that is, in the form of a liquid mixture, a powder mixture or the like, as the case may be. In addition, it can also be distributed in the form of a recovery from fatigue agent, a supplement, a condiment or the like.

A recommended serving of the composition ranges from 1 gram to 100 grams, depending on consumer goals. In one regimen of use, a consumer, upon initiating use of the compound, begins by using 15 ml or gram servings per day, one of which is typically in the morning or before exercising. It will be recognized also that different doses, such as for example, but not limited to, 1 ml to 250 ml per serving, the composition of the present invention can be taken after exercising or just before sleeping periods.

Another embodiment of the present invention is to provide a method for reducing fatigue, improving resistance to fatigue, enhancing endurance to exercise or training, enhancing exercise or training time and distance, or improving recovery time and physiological state from fatigue. The method of the present invention comprises the step of orally absorbing the composition of the present invention as described herein to an individual.

Physical fatigue or muscle weakness (or "lack of strength") is a direct term for the inability to exert force with one's muscles to the degree that would be expected given the individual's general physical fitness.

A test of strength is often used during a diagnosis of a muscular disorder before the etiology can be identified. Such etiology depends on the type of muscle weakness, which can be true or perceived as well as central or peripheral. True weakness is substantial, while perceived rather is a sensation of having to put more effort to do the same task. On the other hand, central muscle weakness is an overall exhaustion of the whole body, while peripheral weakness is an exhaustion of individual muscles.

In addition to physical, fatigue also includes mental fatigue, not necessarily including any muscle fatigue. Such a mental fatigue, in turn, can manifest itself both as somnolence (decreased wakefulness) or just as a general decrease of attention, not necessarily including sleepiness. It may also be described as more or less decreased level of consciousness. In any case, this can be dangerous when performing tasks that require constant concentration, such as driving a vehicle. For instance, a person who is sufficiently somnolent may experience micro sleeps. However, objective cognitive testing should be done to differentiate the neurocognitive deficits of brain disease from those attributable to tiredness.

Temporary fatigue is likely to be a minor illness like the common cold as one part of the sickness behavior response that happens when the immune system fights an infection. Chronic fatigue, on the other hand, meaning of six months or more duration, is a symptom of a large number of different diseases or conditions. Some major categories of diseases that feature fatigue include: Autoimmune diseases such as celiac disease, multiple sclerosis, and spondyloarthropathy; Blood disorders such as anemia and hemochromatosis; Cancer; Chronic fatigue syndrome (CFS); Depression and other mental disorders that feature depressed mood; Eating disorders, which can produce fatigue due to inadequate nutrition; Endocrine disease like diabetes mellitus and hypothyroidism; Fibromyalgia; Heart disease; Infectious diseases such as infectious mononucleosis and influenza; Leukemia or lymphoma; Neurological disorders such as Parkinson's disease and post-concussion syndrome; Physical trauma and other pain-causing conditions, such as arthritis; Pregnancy; and Sleep deprivation or sleep disorders.

Fatigue can be also the result of physical body activity, such as but not necessarily limited to, working, exercising, training, mental stress, overstimulation and under stimulation, jet lag or active recreation, depression, and also boredom, disease and lack of sleep. It may also have chemical causes, such as poisoning or mineral or vitamin deficiencies. Massive blood loss frequently results in fatigue and/or training.

The endurance improver, anti-fatigue composition, motor function improver, energy metabolism activator, muscle strength improver and training endurance enhancer according to the present invention are useful as a food or drug exhibiting an endurance improving effect in sports and also broadly-defined exercises including activities of daily life and labors, an anti-fatigue effect, a motor function improving effect, an energy metabolism activating effect and a muscle strength improving effect. They are also useful as a food or drug having effects of inhibiting reduction in endurance, reduction in energy metabolism and reduction in muscle strength. The composition of the present invention have synergistic combination of collagen hydrolysate, blueberry extract, polyphenol, and licorice extract as effective ingredients which have been separately taken for long years as a food, and have high safety with fewer side effects.

The sense of fatigue is believed to originate in the reticular activating system of the lower brain. Musculoskeletal structures may have co-evolved with appropriate brain structures so that the complete unit functions together in a constructive and adaptive fashion. The entire systems of muscles, joints, and proprioceptive and kinesthetic functions plus parts of the brain evolve and function together in a unitary way.

The present invention will be more readily understood by referring to the following examples which are given to illustrate the invention rather than to limit its scope.

Example I

Anti-Fatigue Supplement 1

The following ingredients are mixed under liquid formula, and then orally given to persons suffering of fatigue at a dosage of 15 ml per day as long as they need.

TABLE 1

Supplement composition 1

| Ingredient | Quantity (kg) range |
| --- | --- |
| Water | 0.4 to 0.9 |
| Collagen hydrolysate | 0.005 to 0.5 |
| Blueberry extract | 0.005 to 0.4 |
| Liquid licorice extract | 0.0005 to 0.1 |

Example II

Anti-Fatigue Supplement Composition 2

The following ingredients are mixed under liquid formula, and then orally given to persons suffering of fatigue at a dosage of 15 ml per day as long as they need.

TABLE 1

Supplement composition 2

| Ingredient | Quantity (kg) range |
| --- | --- |
| Water | 0.4 to 0.9 |
| Glycerin | 0.01 to .3 |
| Glycine | 0.01 to 0.4 |
| Lysine | 0.01 to 0.4 |
| Collagen hydrolysate | 0.005 to 0.5 |
| Poseidogen Kosher | 0.001 to 0.2 |
| Arginine | 0.0005 to 0.2 |
| Glutamine | 0.0005 to 0.2 |
| Sorbate potassium | 0.0005 to 0.2 |
| Sodium benzoate | 0.0005 to 0.3 |
| *Aloe vera* | 0.0001 to 0.02 |
| MSM | 0.001 to 0.2 |
| Blueberry extract | 0.005 to 0.4 |
| Liquid licorice extract | 0.0005 to 0.1 |

Example III

Anti-Fatigue Supplement Formula 3

| Ingredient | Quantity (kg) range |
| --- | --- |
| Water | 0.8 |
| Glycerin | 0.02 |
| Glycine | 0.1 |
| Lysine | 0.07 |
| Collagen hydrolysate | 0.015 |
| Poseidogen Kosher | 0.008 |
| Arginine | 0.001 |
| Glutamine | 0.001 |
| Sorbate potassium | 0.002 |
| Sodium benzoate | 0.005 |
| *Aloe vera* | 0.0007 |
| MSM | 0.01 |
| Blueberry extract | 0.05 |
| Solumine (Liquid liqorice) | 0.001 |

Example IV

Endurance Increasing of Mammals with Supplement Formula 3

Experimental Design

Animals and Exercise Tests

Female CD® IGS rats (n=31 total) aged 11 weeks were randomly divided into two groups. The animals in the test group (n=16) received ad libitum Formula 3 over a 5 week period. Control animals (n=15) were treated identically to test animals, minus access to the product. All animals had ad libitum access to water and chow, and were housed individually allowing us to measure food and drink consumption as well as feces production.

An incremental treadmill exercise performance test was performed on three separate occasions for each animal: in the week preceding supplementation (week 0), and two weeks (week 2) and four weeks (week 4) after onset of supplementation. Animals ran on a Columbus instruments Exer-4/8 treadmill set at a fixed slope of 15° at an initial speed of 10 m/min, followed by an increase of 1 m/min every two minutes, until animals could not maintain the work required (having reached their maximal exercise capacity before fatigue). In this report performance is presented in minutes run.

Statistical Analyses

Data are presented as means±standard errors of the means (SEM). Student t tests were used to compare group mean differences. Repeated measure MANOVAs were used to compare changes to variables over time between groups. All statistical analyses were performed using JMP version 5.0.1.2 software (SAS Institute Inc., Cary, Ind.).

Results

Formula 3 Consumption by Rats

FIG. 1 shows the mean weekly consumption of Formula 3 by rats with ad libitum access to the product. In general, consumption increased from the beginning of the study to reach weekly averages between 50 à 60 mL over the last 3 weeks of supplementation. All rats with access to the product appeared to appreciate to taste and drank it willingly.

TABLE 1

Caloric intake over the first four weeks of Formula 3 supplementation.

|  | Controls | Blue Calorad ® | p |
| --- | --- | --- | --- |
| n | 15 | 12 | — |
| Chow (cal.) | 1979 ± 33 | 1836 ± 44 | 0.013 |
| Formula 3(cal.) | — | 96.7 ± 6.1 | — |
| Total (cal.) | 1979 ± 33 | 1933 ± 44 | 0.4 |

Effects on Exercise Performance

Figure 2:
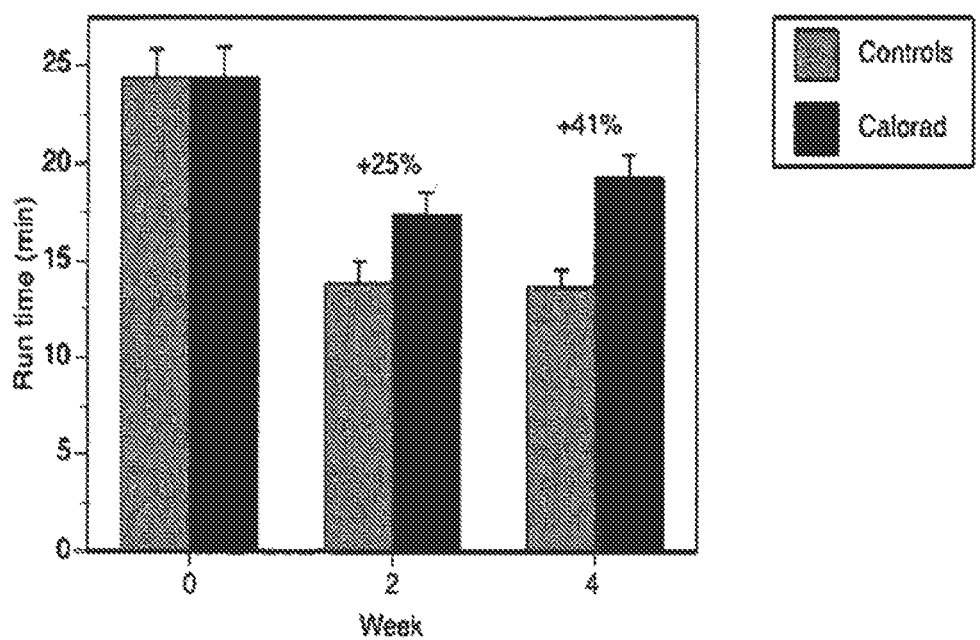
FIG. 2 illustrates the mean treadmill run times to fatigue of rats.

FIG. 2 shows exercise performances of rats from both groups before supplementation (week 0) and after 2 or 4 weeks of supplementation. Before supplementation, no differences in time to fatigue were observed between animals from the two groups. For both groups run times were decreased 2 or 4 weeks later, likely a result of body mass increases in the same time frame. However, rats having access to the supplement demonstrated a much greater exercise capacity than controls. This difference, already evident after 2 weeks of supplementation as 25% longer run times in supplemented animals, was further increased to reach 41% longer run times after 4 weeks of access to Formula 3.

According to their behavior, the rats having ingested the Formula 3 have shown a recovery time 20 percent (from 18 to 14 minutes) lower than the control group.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

I claim:

1. A method for enhancing endurance to and/or promoting recovery from physical exercise in an individual in need thereof comprising orally administering to the individual an effective amount of an oral supplement composition at a rate of at least 1 gram or 1 ml per day, wherein the oral supplement composition comprises:
   (a) about 0.8 kg water,
   (b) about 0.02 kg glycerin,
   (c) about 0.1 kg glycine,
   (d) about 0.07 kg lysine,
   (e) about 0.023 kg collagen hydrolysate,
   (f) about 0.05 kg blueberry extract,
   (g) about 0.001 kg licorice extract,
   (h) about 0.001 kg arginine,
   (i) about 0.001 kg glutamine,
   (j) about 0.002 potassium sorbate,
   (k) about 0.005 kg sodium benzoate,
   (l) about 0.0007 kg aloe vera, and
   (m) about 0.01 kg methylsulfonylmethane.

2. The method of claim 1, wherein said composition is administered to said individual at a rate of about from 1 to 50 ml or 1 to 50 grams per day.

3. The method of claim 1, wherein said individual is a human.

4. The method of claim 1, wherein said collagen hydrolysate has a molecular weight (MW) from 500 to 15,000 Daltons.

5. The method of claim 4, wherein said collagen hydrolysate has a molecular weight (MW) from 1,500 to 5,000 Daltons.

6. The method of claim 1, wherein the oral supplement composition further comprises a salicylate.

* * * * *